United States Patent
Heath et al.

(10) Patent No.: US 9,863,956 B2
(45) Date of Patent: Jan. 9, 2018

(54) DIFFERENTIATION OF ISOBARIC AMINO ACIDS AND OTHER SPECIES

(75) Inventors: James R. Heath, Singapore (SG); Su Seong Lee, Singapore (SG); Jaehong Lim, Singapore (SG); Junhoe Cha, Singapore (SG); Sylvia Tan, Singapore (SG); Shi Yun Yeo, Singapore (SG)

(73) Assignee: Agency for Science, Technology and Research, Singapore (SG)

(*) Notice: Subject to any disclaimer, the term of this patent is extended or adjusted under 35 U.S.C. 154(b) by 793 days.

(21) Appl. No.: 13/386,333

(22) PCT Filed: Jul. 22, 2009

(86) PCT No.: PCT/SG2009/000258
§ 371 (c)(1),
(2), (4) Date: Dec. 17, 2012

(87) PCT Pub. No.: WO2011/010964
PCT Pub. Date: Jan. 27, 2011

(65) Prior Publication Data
US 2013/0109578 A1    May 2, 2013

(51) Int. Cl.
*G01N 33/68* (2006.01)
*C07K 1/04* (2006.01)
(Continued)

(52) U.S. Cl.
CPC ......... *G01N 33/6848* (2013.01); *C07K 1/047* (2013.01); *C07K 1/13* (2013.01);
(Continued)

(58) Field of Classification Search
None
See application file for complete search history.

(56) References Cited

U.S. PATENT DOCUMENTS 5,470,753 A    11/1995 Sepetov et al.
5,510,240 A    4/1996 Lam et al.
(Continued)

FOREIGN PATENT DOCUMENTS

CN    1602422 A    3/2005
CN    1714145 A    12/2005
(Continued)

OTHER PUBLICATIONS

Noren et al, Science, 244(4901), 1989, p. 182-188.*
(Continued)

*Primary Examiner* — Karen S Weiler
(74) *Attorney, Agent, or Firm* — Wolf, Greenfield & Sacks, P.C.

(57) ABSTRACT

Techniques for differentiating isobaric species are described. An isobaric species may be substituted with a tagging species identified using mass spectrometry. The isobaric species may be a subunit of a first polymer having a defined sequence, e.g., the isobaric species may be an amino acid in a protein or a peptide sequence. A tagging species may be substituted for the isobaric species in a second polymer having an otherwise identical sequence as the first polymer. The second polymer may have the same number of sequences as the first polymer, and substantially the same sequence of subunits, with a few exceptions such as the tagging species for the isobaric species. The first polymer and the second polymer may be prepared in the same reaction vessel. A polymer/protein of defined subunit sequence containing an isobaric species or a tagging species may be analyzed by mass spectrometry to determine the sequence.

17 Claims, 11 Drawing Sheets

(51) Int. Cl.
  *C07K 7/06* (2006.01)
  *C40B 50/16* (2006.01)
  *C07K 1/13* (2006.01)
(52) U.S. Cl.
  CPC ............... *C07K 7/06* (2013.01); *C40B 50/16* (2013.01); *G01N 33/6812* (2013.01); *G01N 33/6818* (2013.01); *C07B 2200/11* (2013.01)

(56) References Cited

U.S. PATENT DOCUMENTS

| | | | |
|---|---|---|---|
| 5,650,489 | A | 7/1997 | Lam et al. |
| 5,840,485 | A | 11/1998 | Lebl et al. |
| 5,922,840 | A | 7/1999 | Tomich et al. |
| 6,060,246 | A | 5/2000 | Summerton et al. |
| 6,698,467 | B2 | 3/2004 | Schultz et al. |
| 6,962,818 | B2 | 11/2005 | Schneider et al. |
| 6,998,467 | B1 | 2/2006 | St. George-Hyslop et al. |
| 2002/0168644 | A1 | 11/2002 | Aebersold et al. |
| 2002/0197653 | A1 | 12/2002 | Shair et al. |
| 2004/0072251 | A1 | 4/2004 | Anderson |
| 2006/0134697 | A1 | 6/2006 | Lam et al. |
| 2007/0117101 | A1 | 5/2007 | Sampson et al. |
| 2008/0113875 | A1 | 5/2008 | Chaurand et al. |
| 2012/0122711 | A1 | 5/2012 | Heath et al. |

FOREIGN PATENT DOCUMENTS

| | | |
|---|---|---|
| EP | 0 639 584 | 2/1995 |
| WO | WO-00/26411 A1 | 5/2000 |
| WO | WO-2005/116656 A1 | 12/2005 |
| WO | WO-2007/009457 A2 | 1/2007 |
| WO | WO-2011/008173 A1 | 1/2011 |
| WO | WO-2011/010964 A1 | 1/2011 |
| WO | WO-2012/026887 A1 | 3/2012 |

OTHER PUBLICATIONS

Wang et al. (2001) "Rapid Sequencing of Library-Derived Peptides by Partial Edman Degradation and Mass Spectrometry" J. Comb. Chem 3(3):251-254.*
Wang et al. (2005)"Partial Alloc-Deprotection Approach for Ladder Synthesis of "One-Bead One-Compound" Combinatorial Libraries" J. Comb. Chem. 7 (2):197-209.*
Falciani et al. (2005) "Bioactive Peptides from Libraries" Chemistry & Biology 12(4):417-426.*
Aggarwal et al., Synthesis and screening of a random dimeric peptide library using the one-bead-one-dimer combinatorial approach. Bioconjug Chem. Mar.-Apr. 2006;17(2):335-40. Epub Feb. 8, 2006.
Atherton et al., Peptide synthesis. Part 2. Procedures for solid-phase synthesis using Nalpha-fluorenylmethoxycarbonylamino-acids on polyamide supports. Synthesis of substance P and of acyl carrier protein 65-74 decapeptide. J Chem Soc, Perkin Trans 1. 1981;4(2):538-46.
Bailey et al., DNA-encoded antibody libraries: a unified platform for multiplexed cell sorting and detection of genes and proteins. J Am Chem Soc. Feb. 21, 2007;129(7):1959-67. Epub Jan. 30, 2007.
Cheung et al., A combinatorial approach to identifying protein tyrosine phosphatase substrates from a phosphotyrosine peptide library. J Am Chem Soc. 1997;119(40):9568-9.
Davies et al., Inverted peptides-single bead analysis by methionine scanning and mass spectrometry. Tetrahedron Lett. Dec. 8, 1997;38(49):8565-8.
Ding et al., Two-step fluorescence screening of CD21-binding peptides with one-bead one-compound library and investigation of binding properties of N-(2-hydroxypropyl)methacrylamide copolymer-peptide conjugates. Biomacromolecules. Nov. 2006;7(11):3037-46. Author manuscript available in PMC Sep. 15, 2008 provided. 26 pages.
Edman, Method for determination of the amino acid sequence in peptides. Acta Chemica Scandinavica. 1950;4:283-93.
Holmes et al., Reagents for combinatorial organic synthesis: development of a new o-nitrobenzyl photolabile linker for solid phase synthesis. J Org Chem. Apr. 1995; 60(8):2318-9.
Joo et al., High-throughput sequence determination of cyclic peptide library members by partial Edman degradation/mass spectrometry. J Am Chem Soc. Oct. 4, 2006;128(39):13000-9. Epub Sep. 8, 2006.
Lam et al., A new type of synthetic peptide library for identifying ligand-binding activity. Nature. Nov. 7, 1991;354(6348):82-4. Erratum in: Nature Jul. 30, 1992;358(6385):434. Nature Dec. 24-31, 1992;360(6406):768.
Lam et al., The 'One-Bead-One-Compound' combinatorial library method. Chem Rev. Apr. 1997;97(2):411-48. Epub Apr. 1, 1997.
Lee et al., Rapid microwave-assisted CNBr cleavage of bead-bound peptides. J Comb Chem. Nov. 10, 2008;10(6):807-9. Epub Sep. 24, 2008.
Liu et al., A novel peptide-based encoding system for "one-bead one-compound" peptidomimetic and small molecule combinatorial libraries. J Am Chem Soc. Jul. 3, 2002;124(26):7678-80. Epub Jun. 6, 2002.
Marani et al., Identification of protein-binding peptides by direct matrix-assisted laser desorption ionization time-of-flight mass spectrometry analysis of peptide beads selected from the screening of one bead-one peptide combinatorial libraries. Anal Biochem. Nov. 15, 2007;370(2):215-22. Epub Aug. 9, 2007.
Murata et al., A novel linker for solid-phase synthesis cleavable under neutral conditions. Tetrahedron Letters. Mar. 27, 2006;47(13):2147-50. Epub Feb. 13, 2006.
Naffin et al., Immobilized peptides as high-affinity capture agents for self-associating proteins. Chem Biol. Mar. 2003;10(3):251-9.
Orlando et al., Sequencing membrane proteins by tandem mass spectrometry. Org Mass Spec. Dec. 1993;28(12):1395-1402.
Pastor et al., Redesign of protein domains using one-bead-one-compound combinatorial chemistry. J Am Chem Soc. Dec. 5, 2007;129(48):14922-32. Epub Nov. 9, 2007.
Paulick et al., Cleavable hydrophilic linker for one-bead-one-compound sequencing of oligomer libraries by tandem mass spectrometry. J Comb Chem. May-Jun. 2006;8(3):417-26. Epub Feb. 25, 2006.
Peng et al., Combinatorial chemistry identifies high-affinity peptidomimetics against alpha4beta1 integrin for in vivo tumor imaging. Nat Chem Biol. Jul. 2006;2(7):381-9. Epub Jun. 11, 2006.
Ramage et al., Solid phase peptide synthesis: Fluoride ion release of peptide from the resin. Tetrahedron Letters. 1987;28(35):4105-8.
Rich et al., Preparation of a new o-nitrobenzyl resin for solid-phase synthesis of tert-butyloxycarbonyl-protected peptide acids. J Am Chem Soc. Mar. 19, 1975;97(6):1575-9.
Rink, Solid-phase synthesis of protected peptide fragments using a trialkoxy-diphenyl-methylester resin. Tetrahedron Letters. 1987;28(33):3787-90.
Song et al., A novel and rapid encoding method based on mass spectrometry for "one-bead-one-compound" small molecule combinatorial libraries. J Am Chem Soc. May 21, 2003;125(20):6180-8. Epub Apr. 29, 2003.
St. Hilaire et al., Oligosaccharide mimetics obtained by novel, rapid screening of carboxylic acid encoded glycopeptide libraries. J Am Chem Soc. Dec. 30, 1998;120(51):13312-20. Epub Dec. 11, 1998.
Tornøe et al., Combinatorial library of peptidotriazoles: identification of [1,2,3]-triazole inhibitors against a recombinant Leishmania mexicana cysteine protease. J Comb Chem. May-Jun. 2004;6(3):312-24. Epub Apr. 2, 2004.
Vagner et al., Enzyme-mediated spatial segregation on individual polymeric support beads: application to generation and screening of encoded combinatorial libraries. Proc Natl Acad Sci U S A. Aug. 6, 1996;93(16):8194-9.
Wang, P-alkoxybenzyl alcohol resin and p-alkoxybenzyloxycarbonylhydrazide resin for solid phase synthesis of protected peptide fragments. J Am Chem Soc. Feb. 21, 1973;95(4):1328-33.

(56) References Cited

OTHER PUBLICATIONS

Wu et al., Identifying substrate motifs of protein kinases by a random library approach. Biochemistry. Dec. 13, 1994;33(49):14825-33.
Yu et al., Combinatorial epitope search: pitfalls of library design. Bioorg Medic Chem Lett. Jan. 7, 1997;7(1):95-8.
Hu et al., Method for screening and MALDI-TOF MS sequencing of encoded combinatorial libraries. Anal Chem. Oct. 1, 2007;79(19):Supplemental Information S1-33. Epub Aug. 23, 2007.
Extended European Search Report dated Oct. 5, 2012 in connection with EP 09847626.0.
Agnew et al., Iterative in situ click chemistry creates antibody-like protein-capture agents. Angew Chem Int Ed Engl. Jun. 22, 2009;48(27):4944-8. Epub Mar. 19, 2009.
Lee et al., Accurate MALDI-TOF/TOF sequencing of one-bead-one-compound peptide libraries with application to the identification of multiligand protein affinity agents using in situ click chemistry screening. Anal Chem. Jan. 15, 2010;82(2):672-9. Epub Dec. 14, 2009.
Thieriet et al., Solid-phase peptide synthesis in the reverse (N→ C) direction. Org Lett. Jun. 29, 2000;2(13):1815-7. Epub Jun. 7, 2000.
U.S. Appl. No. 13/384,510, filed Jan. 17, 2012, Heath et al.
EP 10800125.6, Feb. 4, 2013, Extended European Search Report.
Aebersold et al., Mass spectrometry-based proteomics. Nature. vol. 422, No. 6928, 2003, pp. 198-207.
Colzani et al., Relative Protein Quantification by Isobaric SILAC with Immonium Ion Splitting (ISIS)*. Mol Cell Proteomics. vol. 7, No. 5, 2008, pp. 927-937.
Gogichaeva et al., MALDI TOF/TOF tandem mass spectrometry as a new tool for amino acid analysis. J Am Soc Mass Spectrom. Feb. 2007;18(2):279-84. Epub Oct. 30, 2006.
Hu et al., Method for Screening and MALDI-TOF MS Sequencing of Encoded Combinatorial Libraries. Anal Chem. vol. 79, No. 19, 2007, pp. 7275-7285.
International Preliminary Report on Patentability dated Nov. 9, 2011 in connection with PCT/SG2009/000258.
International Preliminary Report on Patentability dated Oct. 27, 2011 in connection with PCT/SG2010/000266.
International Search Report and Written Opinion dated Oct. 19, 2010 in connection with PCT/SG2010/000266.
International Search Report and Written Opinion dated Oct. 7, 2009 in connection with PCT/SG2009/000258.
Invitation to Pay Additional Fees dated Sep. 10, 2010 in connection with PCT/SG2010/000266.
Lee et al., Rapid and robust sequencing of one-bead-one-compound peptide libraries by MALDI-TOF/TOF. Abstracts of Papers, 238th Am Chem Soc Nat Meeting 2009, Published online Jun. 22, 2009, Retrieved from the internet Apr. 9, 2012: <http://oasys2.confex.com/acs/238nm/techprogram/P1277427.HTM>.
Salmon et al., Use of large combinatorial chemical libraries for anticancer drug discovery. International J of Pharmacognosy. 1995;33, Supplement:67-74.
Shchepinov et al., Steric factors influencing hybridisation of nucleic acids to oligonucleotide arrays. Nucleic Acids Res. Mar. 15, 1997;25(6):1155-61.
Wang et al., Partial Alloc-Deprotection Approach for Ladder Synthesis of "One-Bead One-Compound" Combinatorial Libraries. J Comb Chem. vol. 7, No. 2, 2005, pp. 197-209.
Written Opinion dated Jan. 12, 2011 in connection with PCT/SG2009/000258.
Written Opinion dated Nov. 30, 2010 in connection with PCT/SG2009/000258.
Written Opinon dated Aug. 12, 2011 in connection with PCT/SG2010/000266.
Written Opinon dated Jun. 1, 2011 in connection with PCT/SG2010/000266.
Youngquist et al., Generation and screening of combinatorial peptide libraries designed for rapid sequencing by mass spectrometry. J Am Chem Soc. Apr. 1995; 117(14):3900-906.
Extended European Search Report dated Feb. 4, 2013 for EP 10800125.6.
Robins et al., On-bead combinatorial techniques for the identification of selective aldose reductase inhibitors. Bioorg Med Chem. Dec. 1, 2006;14(23):7728-35. Epub Aug. 22, 2006.

* cited by examiner

Fig. 3

| m/z | Sequence | | | | | | | SEQ ID NO: |
|---|---|---|---|---|---|---|---|---|
| 990.613 | L | H | R | Y | R | R | Y | 10 |
| 983.605 | L | H | R | Y | R | L | R | 11 |
| 1013.546 | L | H | R | Y | W | R | R | 12 |
| 955.619 | L | H | R | Y | R | R | K | 13 |
| 1004.536 | L | H | R | Y | W | R | F | 14 |
| 1013.523 | L | H | R | Y | W | R | R | 12 |
| 955.559 | L | H | R | Y | L | R | Q | 15 |
| 1004.494 | L | H | R | Y | W | R | F | 14 |
| 940.547 | L | H | R | Y | L | R | Y | 16 |
| 1020.544 | L | H | R | Y | W | W | R | 17 |
| 1013.672 | L | H | R | Y | W | R | R | 12 |
| 1013.56 | L | H | R | Y | W | R | R | 12 |
| 985.51 | L | H | R | Y | W | K | W | 18 |
| 985.53 | L | H | R | Y | W | Y | S | 19 |
| 985.56 | L | H | R | Y | W | Y | S | 19 |
| 1004.502 | W | R | R | Y | W | R | F | 14 |
| 1071.568 | W | R | R | R | W | K | W | 20 |
| 1036.54 | W | R | R | R | Y | Y | R | 21 |
| 1077.582 | W | R | R | R | W | K | K | 22 |
| 1061.596 | W | R | R | Y | Y | Y | F | 23 |
| 1014.625 | W | R | R | K | K | F | K | 24 |
| 1022.599 | W | R | R | H | Y | Y | Y | 25 |
| 1049.553 | W | R | R | K | W | R | K | 26 |
| 985.596 | K | – | Y | R | Y | Y | V | 27 |
| 972.551 | K | – | R | Y | K | Y | R | 28 |
| 1004.63 | – | Q | H | R | R | F | F | 29 |
| 911.531 | K | Y | F | Y | Y | Y | W | 1 |
| 953.546 | Y | K | R | K | K | K | F | 30 |
| 1045.558 | Y | K | R | Y | Y | Y | F | 31 |

| m/z | Sequence | | | | | | | SEQ ID NO: |
|---|---|---|---|---|---|---|---|---|
| 958.547 | V | K | Y | R | F | Y | 32 |
| 999.57 | R | R | F | Q | F | Y | 33 |
| 1032.6 | L | R | W | R | Y | R | 34 |
| 989.57 | Y | R | W | L | R | L | 35 |
| 1045.555 | Y | R | Y | W | F | Y | 36 |
| 936.558 | Y | K | F | F | R | R | 37 |
| 958.67 | K | R | R | R | R | R | 38 |
| 1049.634 | R | R | H | R | R | H | 39 |
| 1002.645 | R | Q | Y | R | Y | R | 40 |
| 1019.486 | K | R | H | H | Y | F | 41 |
| 1051.677 | R | R | Y | R | W | R | 42 |
| 1019.532 | V | R | W | L | K | K | 43 |
| 1000.53 | R | Q | R | K | Y | L | 44 |
| 867.584 | R | R | F | Y | R | Q | 45 |
| 1000.537 | W | L | R | R | Q | K | 46 |
| 946.602 | Y | R | R | R | R | K | 47 |
| 952.572 | W | L | Y | L | F | R | 48 |
| 1075.627 | W | Y | Y | K | R | Y | 49 |
| 1008.604 | W | W | R | R | R | H | 50 |
| 987.567 | Y | Y | Y | H | F | Y | 51 |
| 1000.569 | L | R | R | Q | W | H | 52 |
| 1039.554 | Y | R | R | Y | Y | R | 53 |
| 962.526 | R | – | – | – | K | R | 54 |
| 1093.538 | W | Y | Y | R | Y | W | 55 |
| 1135.553 | W | W | Y | Y | K | 56 |
| 1000.474 | Y | H | R | K | Y | R | 57 |
| 1005.538 | L | Q | Y | Q | – | K | 58 |
| 938.565 | Y | R | R | R | R | H | 59 |
| 990.528 | R | Y | R | Y | R | 60 |
| 1012.63 | W | W | W | R | R | L | 61 |

| m/z | SEQUENCE | | | | | | SEQ ID NO: |
|---|---|---|---|---|---|---|---|
| 955.53 | H | I | R | Y | K | R | 2 |
| 1038.666 | R | R | R | R | R | R | 62 |
| 945.645 | K | K | K | R | F | R | 63 |
| 992.613 | L | Y | K | K | R | W | 64 |
| 987.575 | Y | K | Y | R | F | K | 65 |
| 1059.608 | R | Y | R | Y | R | Y | 66 |
| 1036.604 | R | R | Y | R | F | R | 67 |
| 997.531 | R | L | K | W | R | R | 68 |

Fig. 5

DIFFERENTIATION OF ISOBARIC AMINO ACIDS AND OTHER SPECIES

RELATED APPLICATIONS

This application is a U.S. National Stage application under 35 U.S.C. §371 based on International Application No. PCT/SG2009/000258, filed Jul. 22, 2009, the contents of which is incorporated herein by reference in its entirety.

FIELD OF INVENTION

This invention relates generally to differentiating isobaric species. In some embodiments, isobaric amino acids are differentiated.

BACKGROUND OF INVENTION

Split-and-mix synthesis approaches have been used to produce peptide libraries on small beads, with each bead containing an individual peptide molecule. Such libraries are referred to as one-bead-one-compound (OBOC) libraries. A common use of OBOC libraries is to identify molecules from the libraries that perform some function of interest. As an example, an OBOC library may be used to identify a molecule (i.e., a peptide) that binds to a particular protein by screening the library for beads that are associated with the protein ("hit" beads). The hit beads can be separated from the rest of the library, and the identity of the peptide on a particular hit bead can be determined using a peptide sequencing strategy.

Peptide sequencing using mass spectrometry is complicated by the existence of amino acids with similar masses (e.g., isobaric amino acids) that cannot be differentiated by mass spectrometry. Thus, a need exists for methods for differentiating isobaric amino acids.

SUMMARY OF INVENTION

This invention relates generally to methods for differentiating isobaric species. In some embodiments, isobaric amino acids are differentiated. The subject matter of the present invention involves, in some cases, interrelated products, alternative solutions to a particular problem, and/or a plurality of different uses of one or more systems and/or articles.

In one aspect, the invention is directed to a method. In one set of embodiments, the method includes an act of growing amino acid sequences on a surface. In some cases, at least one of the amino acids within the amino acid sequence is an isobaric amino acid. In certain embodiments, when the isobaric amino acid is added to a medium exposed to the sequences for addition thereto, the medium containing the isobaric amino acid further contains an entity, incorporatable in an amino acid sequence, that has a molecular weight different than the isobaric amino acid.

In another set of embodiments, the method includes an act of distinguishing, using mass spectrometry, a first amino acid sequence from a second amino acid sequence having the same number of amino acid residues as the first sequence. In some embodiments, the second amino acid sequence is identical to the first amino acid sequence except at one or more locations where the first amino acid sequence contains a first, isobaric amino acid. In some cases, the second amino acid sequence contains a second amino acid that has a molecular weight different than the first amino acid.

According to yet another set of embodiments, the method includes an act of exposing an amino acid sequence, attached to a surface, to a solution containing an isobaric amino acid. In some embodiments, the isobaric amino acid is a member of an isobaric group consisting of a first amino acid species and a second amino acid species. In certain instances, when the isobaric amino acid incorporated into the amino acid sequence is the first amino acid species, the solution further comprises an entity, incorporatable in an amino acid sequence, that has a molecular weight different than the isobaric amino acid. In some cases, when the isobaric amino acid is incorporated into the amino acid sequence is the second amino acid species, the solution is substantially free of the incorporatable entity.

The invention, in another aspect, is directed to a composition. In one set of embodiments, the composition includes a first amino acid sequence and a second amino acid sequence having the same number of amino acid residues as the first sequence. In some cases, the second amino acid sequence is identical to the first amino acid sequence except at one or more locations where the first amino acid sequence contains a first, isobaric amino acid. In certain instances, the second amino acid sequence contains a second amino acid that has a molecular weight different than the first amino acid.

The invention, in yet another aspect, is directed to an article. According to one set of embodiments, the article includes a surface to which is attached a first amino acid sequence and a second amino acid sequence, each via a cleavable moiety. In some embodiments, the second amino acid sequence has the same number of amino acid residues as the first sequence. In certain instances, the second amino acid sequence is identical to the first amino acid sequence except at one or more locations where the first amino acid sequence contains a first, isobaric amino acid. In some instances, the second amino acid sequence contains a second amino acid with a molecular weight different from the first amino acid.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 3 shows a table of hit peptides and the corresponding parent peak masses in accordance with an embodiment of the invention;

FIG. 5 shows a table of hit sequences generated from the screening of an OBOC hexamer peptide library with bCAII in accordance with one embodiment of the invention;

DETAILED DESCRIPTION

Figure 1A:
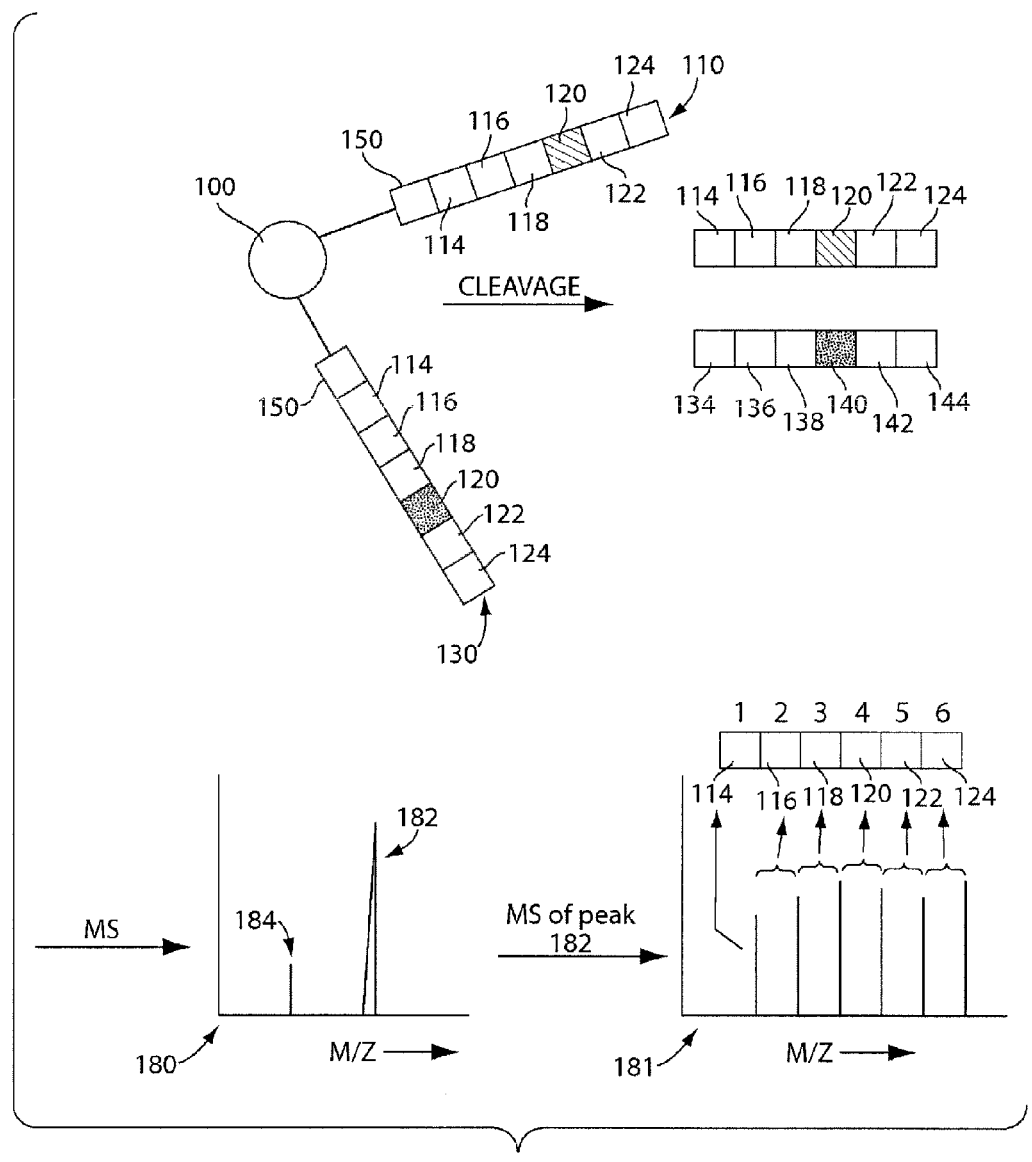
FIG. 1A shows an analysis method in accordance with an embodiment of the invention.

Techniques for differentiating isobaric species are described. In one aspect, an isobaric species is substituted with a tagging species that can be identified using mass spectrometry. The isobaric species may be a subunit of a first polymer having a defined sequence, e.g., the isobaric species may be an amino acid in a protein or a peptide sequence. A tagging species may be substituted for the isobaric species in a second polymer having an otherwise identical sequence as the first polymer. For instance, the second polymer may have the same number of sequences as the first polymer, and substantially the same sequence of subunits, with a few exceptions such as the tagging species for the isobaric species. In some embodiments, the first polymer and the second polymer are prepared essentially simultaneously in the same reaction vessel. A polymer (such as a protein) having a defined subunit sequence and containing an isobaric species or a tagging species may be analyzed by mass spectrometry to determine the sequence of the polymer.

In one aspect, the invention allows for the determination of unknown entities, such as proteins or peptides. For example, the unknown entities may be peptide sequences, some of which interact with a protein target of interest and some of which do not. The unknown entities may be exposed to a protein target of interest and by separating the unknown entities that bind to or otherwise interact with the protein target of interest from sequences that do not and analyzing the binding or interacting unknown entities (e.g., using mass spectrometry), information regarding the unknown entity may be obtained. However, in some cases, some of the unknown entities may contain isobaric species, such as isobaric amino acids, which cannot be adequately distinguished using certain techniques, such as certain mass spectrometry techniques.

Isobaric species are species having different molecular structures, but having a mass that cannot be distinguished. For instance, the isobaric species may be structural isomers of each other, or contain different atoms that nevertheless sum to the same atomic mass. An isobaric group member refers to a composition that cannot be distinguished from other members of the isobaric group (e.g., two amino acids having the same mass). Examples of isobaric groups include leucine/isoleucine and glutamine/lysine. An isobaric group member may be any type of composition. For example, the isobaric group member may be a single molecule (i.e., an amino acid, a nucleoside, a sugar, etc.) or a group of molecules (i.e., a dimer, trimer, tetramer, etc.).

In some cases, isobaric species may not be distinguishable from other members of the isobaric group after undergoing a chemical transformation. That is, the isobaric species may not be sufficiently distinguishable after undergoing a chemical transformation. For example, two members of an isobaric group may or may not be isobaric (i.e., distinguishable by mass) when incorporated into a polymer; however, upon analysis by a technique such as mass spectrometry, one or more of the isobaric group members may undergo a chemical transformation (i.e., fragmentation, ionization, etc.) such that they cannot be distinguished from one another on the basis of mass. It should be understood that in some embodiments, some species that may be isobaric when analyzed by a first technique, may not necessarily be isobaric when analyzed by a second technique.

A non-limiting example will now be described. FIG. 1A shows a particle 100 having a probe entity 110 and a tagging entity 130 attached to the surface of the particle via a linker 150. It should be understood that although particles are described in FIG. 1A, this is by way of example only, and in other embodiments, other systems may be used, e.g., the probe entity and tagging entity may be in solution, attached to a planar substrate, or the like. Probe entity 110 comprises a sequence of subunits chosen from a pool of subunits and includes an isobaric group member 120 (i.e., isobaric group member 120 has the same mass as one or more other subunits in the pool of subunits). Tagging entity 130 comprises an identical sequence of subunits as probe entity 110, except that the isobaric group member is substituted with a tagging species 140 having a mass different than that of the isobaric group member 120. The tagging species codes for the presence of the isobaric group member 120 in the probe entity 110. The probe entity and tagging entity may be cleaved from the particle, e.g., via linker 150, as described in more detail below, to form a mixture that is subsequently analyzed by mass spectrometry (or other techniques) to produce a mass spectrum 180. Since the probe entity and tagging entity differ only by the presence of the isobaric group member and tagging species, respectively, the mass spectrum of the mixture shows a parent peak 182 for the probe entity that differs in mass from the parent peak 184 for the tagging entity by an amount generally equal to the difference in mass between the isobaric group member and tagging species. Thus, in this example, the presence of two peaks having this mass difference indicates the presence of an isobaric group member in the probe entity. The parent peak 182 for the probe entity is then fragmented and mass analyzed to determine the sequence of the probe entity (mass spectrum 181). Spectrum 181 shows the fragments of peptide 160 in order of increasing mass from left to right. Generally, the difference in mass between the peaks indicates the mass of the subunits in the probe entity and allows the subunits to be identified, e.g., using known or readily available techniques.

Figure 1B:
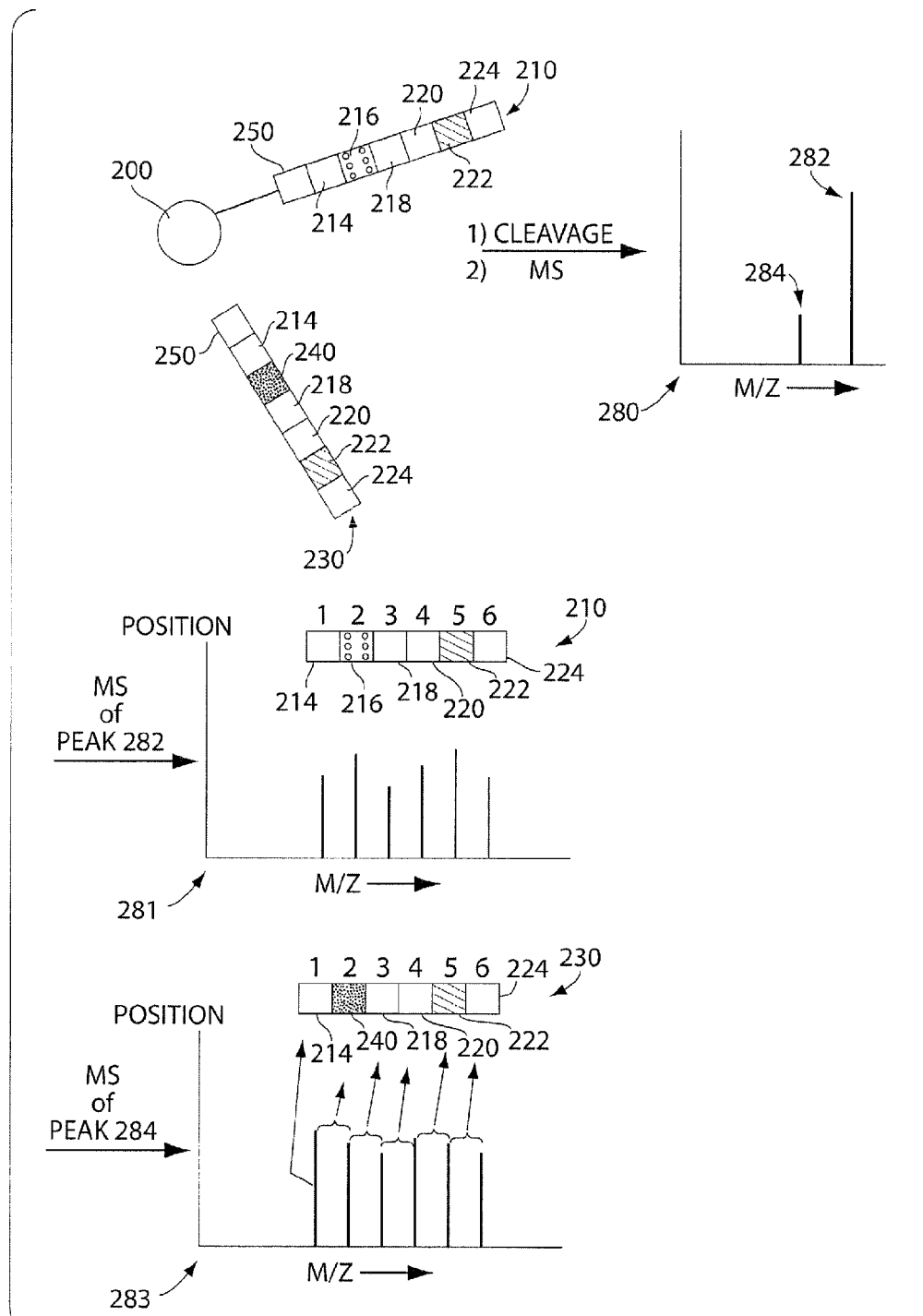
FIG. 1B shows an analysis method in accordance with another embodiment of the invention.

In another non-limiting example, a probe entity containing two or more isobaric group members can be sequenced using tandem mass spectrometry. Referring now to FIG. 1B, a particle 200 is shown having a probe entity 210 and a tagging entity 230 attached to the surface of the particle via a linker 250. Probe entity 210 comprises a sequence of subunits chosen from a pool of subunits and includes two isobaric group members 216 and 222 having the same mass but differing in chemical structure. Tagging entity 230 comprises an identical sequence of subunits except that the isobaric group member 216 is substituted with a tagging species 240 having a mass different than that of the isobaric group members 216 and 222. The tagging species codes for the presence of the isobaric group member 216 in the probe entity 210. The probe entity and tagging entity may be cleaved from the particle to form a mixture that is subsequently analyzed by mass spectrometry to produce a mass spectrum 280. The mass spectrum of the mixture shows a parent peak 282 for the probe entity that differs in mass from the parent peak 284 for the tagging entity by an amount equal to the difference in mass between the isobaric group member and tagging species. Sequencing of the parent peak 282 (i.e., probe entity 210) by fragmentation (spectrum 281) indicates the positions of the two isobaric group members but does not distinguish them from each other. Sequencing of the parent peak 284 (i.e., tagging entity 230) by fragmentation (spectrum 283) reveals that position 2 has a different mass than the isobaric group members indicating that isobaric group member 216 is in position 2 and isobaric group member 222 is in position 4.

Accordingly, based on the differences in mass spectrometry data and knowledge of the particles and their probe and tagging entities, a polymer, such as a peptide or protein, may be analyzed using mass spectroscopy or other techniques to determine sequences containing, or suspected of containing, isobaric species such as isobaric amino acids. Thus, after a subset of particles and their probes are collected, e.g., upon interaction or reaction with an unknown entity, the probes may be analyzed to determine the sequences of the probes, and thus, information (e.g., sequence information) regarding the unknown entity.

Thus, in some instances, particles that are at least suspected of containing isobaric species may be analyzed as follows. One non-limiting example of a suitable technique with reference to a logic tree analysis flow chart used to analyze mass spectrometry data is provided in FIG. 1C. In this example, the probe entity and the tagging entity are peptides, but it should be understood that other probe entities and tagging entities may also be analyzed in analogous fashion. The flow chart of this example begins with the acquisition of a mass spectrum (MS spectrum) for an isolated peptide sample. The mass spectrum is analyzed for the parent peak of the probe entity and for any additional peaks (i.e., a tagging entity parent peak). In some embodiments, the probe entities and tagging entities are members of a library of entities for which all possible masses are known. Thus, the parent peak of the probe entity can be identified, for example, by comparison to a list of possible masses for probe entities. Likewise the parent peak of a tagging entity can also be identified. If no peak is present in addition to the probe entity parent peak, then the parent peak may be sequenced to determine the identity of the parent peak (i.e., the parent peak of the peptide may be fragmented to determine the amino acid sequence). Since no tagging entity was present, this indicates that the probe entity either (1) contained no isobaric amino acids or (2) contained an isobaric amino acid that was not coded by a tagging species. For example, for the isobaric amino acid pair leucine and isoleucine, leucine may be coded by alanine and isoleucine may not be coded. Thus, if the mass spectrum of a peptide sample does not have a second parent peak corresponding to a tagging entity, then the probe entity contains isoleucine or does not contain an isobaric amino acid. Conversely, if the mass spectrum reveals a second parent peak corresponding to a tagging entity, then the probe entity contains leucine.

Figure 1C:
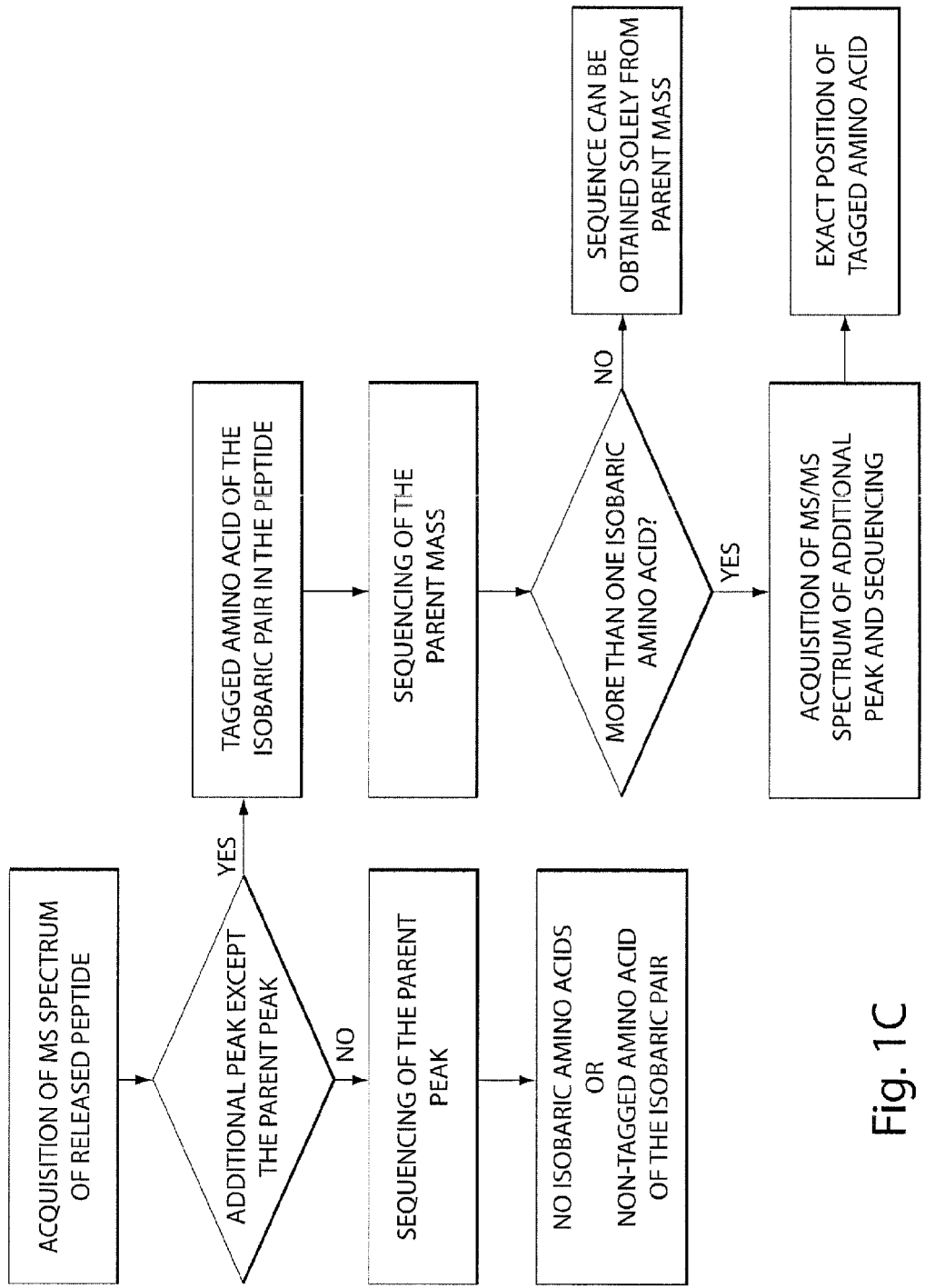
FIG. 1C shows a logic tree analysis flow chart in accordance with one embodiment of the invention.

Still referring to FIG. 1C, if a second parent peak in addition to the probing entity parent peak is present, this indicates the presence of a tagging species in the second parent peak corresponding to an isobaric amino acid in the probe entity. The first parent peak is then sequenced. If more than one isobaric amino acid is not present in the probe entity, then the sequence of the probe entity can be obtained solely from sequencing the parent mass of the probe entity. However, if more than one isobaric amino acid is present in the probe entity, then the tagging entity is sequenced to determine the position of the tagging species (i.e., the tagged amino acid). In some cases, this may be repeated if yet more isobaric amino acids are present in the probe entity.

Any suitable techniques may be used to determine the mass of an entity, for example, mass spectrometry, mass sedimentation, or the like. Any mass spectrometry technique may be used in embodiments involving mass spectrometry. For example, techniques such as MALDI, ESI, FAB, etc. may be used to ionize a species. The mass of an ionized analyte may be determined using analyzers such as time-of-flight (TOF), quadrupole, Fourier transform ion cyclotron resonance, orbitrap, sector field, etc. In some embodiments, an ion may be fragmented to produce secondary ions. The secondary ions may also be fragmented, for example using a technique such as tandem mass spectrometry. For instance, methods such as collision-induced dissociation, electron capture dissociation, electron transfer dissociation, infrared multiphoton dissociation, blackbody infrared radiative dissociation, and the like may be used to fragment ions.

A probe entity may be any composition that can contain an isobaric group member. For example, a probe entity may contain subunits. In some embodiments, the probe entity may be a peptide and the subunits may be amino acid residues of the peptide. The peptide may comprise any amino acid, including alanine, cysteine, aspartic acid, glutamic acid, phenyalanine, glycine, histidine, isoleucine, lysine, leucine, methionine, arparagine, pyrrolysine, proline, glutamine, arginine, serine, threonine, selenocysteine, valine, tryptophan, tyrosine, etc. Other amino acids, including non-naturally-occurring amino acids may also be used in some cases, and in some embodiments the non-naturally-occurring amino acids may also be isobaric, e.g., with other non-naturally-occurring amino acids and/or with naturally occurring amino acids. Thus, the peptide may be modified using techniques known in the art. For example, the peptide may be modified at the N-terminus and/or the C-terminus. The side groups of the amino acids may also be modified. In some cases, the backbone of the peptide may be modified. In some embodiments, the peptide may be linked to another polymer, for example a biological polymer such as a nucleic acid and/or a polysaccharide. The peptide may also be linked to other polymers, for example polyesters (e.g., polylactide, polyglycolide, PLGA, polycaprolactone, etc.), polyamides, polyurethanes, polyanhydrides, etc. and combinations thereof.

An "amino acid" is given its ordinary meaning as used in the field of biochemistry. An isolated amino acid typically, but not always (for example, as in the case of proline) has a general structure $NH_2$—CHR—COOH. R may be any suitable moiety; for example, R may be a hydrogen atom, a methyl group, or an isopropyl group. A series of isolated amino acids may be connected to form a peptide or a protein by reaction of the —$NH_2$ of one amino acid with the —COOH of another amino acid to form a peptide bond (—CO—NH—). In such cases, each of the R groups on the peptide or protein can be referred to as an amino acid residue. The amino acid may be one of the 20 amino acids commonly found in nature (the "natural amino acids"), or an unnatural amino acid, i.e., an amino acid that is not one of the natural amino acids. Non-limiting examples of unnatural amino acids include alloisoleucine, allothreonine, homophenylalanine, homoserine, homocysteine, 5-hydroxylysine, 4-hydroxyproline, 4-carboxyglutamic acid, cysteic acid, cyclohexylalanine, ethylglycine, norleucine, norvaline, 3-aminobutyric acid, beta-amino acids (e.g., beta-alanine), N-methylated amino acids such as N-methylglycine, N-methylalanine, N-methylvaline, N-methylleucine, N-methylisoleucine, N-methylnorleucin, N-methyl-2-aminobutyric acid, N-methyl-2-aminopentanoic acid, etc., as well as the D-isomers of the natural amino acids.

The tagging entity may be identical to a probe entity, or in other instances, the tagging entity may differ from the probe entity in one or more places. For example, a tagging entity may comprise the same subunits arranged in the same order but differing from a probe entity in that one or more of the corresponding subunits is substituted with a tagging species. For example, a peptidic probe entity may contain a first amino acid from an isobaric group containing the first amino acid and a second amino acid, and a tagging species having a distinguishable mass from the isobaric group members may be substituted for the first amino acid (i.e., the tagging species "codes" for the first amino acid). In some embodiments, a first tagging species may be substituted for a first amino acid and a second tagging species may be substituted for a second amino acid.

A tagging species may be any composition that can distinguish a member of an isobaric group (e.g., by a difference in mass). In some embodiments, the tagging species may be a composition incorporatable into a polymer. For example, the tagging species may be an amino acid, a nucleoside, a saccharide, and the like. In some embodiments, a tagging species may be a composition that may be substituted for a subunit in a polymer but does not belong to the same chemical group as the other subunits in the polymer. For example, the tagging species may have an amino group and a carboxyl group such that it can be incorporated into a peptide but may not be an amino acid.

In some cases, a probe entity and a tagging entity may be attached to a surface, e.g., the surface of a particle, the surface of a planar substrate, etc. The entities may be attached by any suitable method. For example, the surface may have a functional group attached thereto to which a probe entity and/or tagging entity may be connected. An entity may be connected to a surface using a covalent bond, an ionic bond, van der Waals forces, hydrophobic interactions, etc. Chemical bonds such as esters, amides, ethers, anhydrides, urethanes, etc. may be used to attach an entity to a surface. In some embodiments, a metal-sulfur bond (i.e., gold-sulfur) may be used to attach an entity to a surface.

In some embodiments, a cleavable linker may be used to connect an entity to a surface (i.e., a particle). Such linkers are known to those skilled in the art, for example in solid-phase peptide synthesis and solid-phase oligonucleotide synthesis. In some instances, a methionine residue may be used as a linker. A methionine linker may be cleaved by a reagent such as CNBr, which cleaves peptide bonds at the C-terminus of methionine residues. Examples of other types of linkers that may be used include acid-cleavable linkers, base-cleavable linkers, photo-cleavable linkers, and redox-cleavable linkers such as those mediated by periodate, 2,3-Dichloro-5,6-Dicyanobenzoquinone (DDQ), cerium (IV) ammonium nitrate (CAN), etc. The cleavable linker may be susceptible to cleavage under conditions that are essentially benign to the entity. In other embodiments, the entity may be cleaved at one or more places in addition to being cleaved at the linker.

In some aspects, a probe entity and a tagging entity may be synthesized essentially simultaneously. For example, in the instance of peptide entities, solid-phase synthesis techniques known to those skilled in the art may be used to synthesize a probe entity and a tagging entity essentially simultaneously by sequentially adding amino acid residues to a growing peptide chain in the same reaction vessel. When it is desired to add a specific non-isobaric amino acid to a peptide chain, the peptide chain may be exposed to a reaction mixture containing essentially one non-isobaric amino acid. By contrast, to add an isobaric amino acid to a peptide chain that has been assigned a tagging species (i.e., another amino acid having a different mass), the peptide may be exposed to a reaction mixture containing a combination of the isobaric amino acid and the tagging species. The ratio of isobaric amino acid to tagging species may be any suitable ratio, e.g., less than about 100:1, less than about 10:1, less than about 5:1, less than about 2:1, less than about 1:1, less than about 1:2, less than about 1:5, less than about 1:10, less than about 1:100, etc.

In some instances, a library of probe entities and tagging entities may be prepared. In some instances the library of entities may be attached to particles (i.e., beads). For example, a one-bead-one-compound (OBOC) library may be generated in one embodiment. An OBOC library generally contains a plurality of beads where each bead is attached to one or more copies of a single compound (i.e., a probe entity). For example, a first bead may be attached to a first peptide having a first sequence and a second bead may be attached to a second peptide having a second sequence, which is typically different from the first sequence. In this example, it should be understood that each of the beads also may be attached to a tagging entity corresponding to the probe entity attached to the bead. A peptide OBOC library may be generated according to split-and-pool synthesis techniques known to those skilled in the art.

In some embodiments, it may be desired to know which, if any, of the library members interact with a target of interest (i.e., a protein). The library members may be contacted with a suitable target of interest, and members that bind to the target of interest may be enriched using techniques known in the art, such as fluorescence sorting. This process may be repeated one or more times in order to narrow the number of "hits" (i.e., library members that bind to the target). The isolated hits may then be subjected to the methods described above to determine the identity of the hits. Targets of interest include biopolymers such as proteins, nucleic acids, and polysaccharides, and specific compositions such as The following examples are provided for illustration purposes and are not intended to be limiting.

Example 1

This example demonstrates synthesis of an OBOC hexamer peptide library. "Split-and-mix" synthesis of a peptide library was performed using an automatic synthesizer (Titan 357, AAPPTEC). TentaGel S Amino beads (2.2 g, 90 micron diameter, loading of $NH_2$: 0.24 mmol/g) were swelled in NMP (27 ml) for 2 hr in a Collective Vessel (CV). For incorporation of 100% methionine as a linker, fmoc-Met (2 equiv, 0.2 M solution in NMP) was added to the CV, as well as TBTU (2 equiv, 0.2 M solution in NMP), and DIEA (5 equiv, 0.5 M solution in NMP), after draining the solvent. The resulting mixture was vortexed for 30 min. The solution was drained and the coupling step was repeated by using fresh reagent solutions. The resulting beads were thoroughly washed by NMP (27 ml×4). Next, 20% piperidine in NMP (27 ml) was added and the CV was vortexed for 5 min. The liquid was drained and a fresh solution of 20% piperidine in NMP (27 ml) was added, and the CV was vortexed for another 15 min. The resulting beads were thoroughly washed by NMP (27 ml×4) and DCM (27 ml×4), followed by distribution equally into 11 Reaction Vessels (RV). One of the 11 selected Fmoc-protected D-amino acids as diversity elements (F, H, K, L, R, S, V, W, Y, 9:1 mixture of Q and G, and 9:1 mixture of I and A, 3 equiv each), TBTU (3 equiv) and DIEA (7.5 equiv) were added to each RV. The RV was then vortexed for 30 min. After draining the solution, the coupling step was repeated. The resulting beads in each RV were washed by NMP (2 ml×4). Again, 20% piperidine in NMP (2 ml×4) was added to each RV, which was vortexed for 15 min. The liquid was drained and a fresh solution of 20% Piperidine in NMP (2 ml×4) was added with vortexing for another 30 min. Beads in each RV were thoroughly washed by NMP (2 ml×4) and DCM (2 ml×4), which were combined into the CV. The overall split, coupling, deprotection, and mix processes were repeated until the beads appended a hexamer, excluding the initial methionine. The beads were transferred to a 50 ml reactor equipped with a filter. The protective groups in the residues were removed by shaking in TFA-water-TIS (27 ml, 94:3:3, v/v) for 2 h. The liquid was drained and the resulting beads were thoroughly washed by DCM (27 ml×3), methanol (27 ml×3), water (27 ml×3), methanol (27 ml×3), DCM (27 ml×3), and diethylether (27 ml), successively, and then dried under reduced pressure for 24 h.

Example 2

This example demonstrates library screening. Alexa Fluor® 647 protein labeling kit (A20173, Invitrogen) was chosen as the reactive dye for labeling bovine carbonic anhydrase (bCAII) following the supplier's protocol. Briefly, 2 mg/mL of bCAII in 0.1 M sodium bicarbonate (pH ~8.3) was transferred 0.5 mL of bCAII solution into the vial of the reactive dye, and the vial was capped and inverted several times to dissolve the dye completely. The reaction mixture was stirred for 1 hr at room temperature under dark conditions. The Alexa Fluro® 647 labeled bCAII (bCAII-A647) was purified from the mixture using the size exclusion purification resin in the kit. Purified and labeled bCAII-A647 was characterized by NanoDrop (Thermo Scientific) and gel documentation (Typhoon) after SDS-PAGE. Dried library resin (200 mg) was transferred into an 8 mL Alltech vessel and pre-incubated in blocking solution, 0.05% $NaN_3$, 0.1% Tween 20 and 0.1% BSA in PBS buffer (pH 7.4) for 1 hr on a 360° shaker at room temperature. The buffer solution was drained by vacuum and then 5 mL of 50 nM dye labeled bCAII diluted in blocking solution was added to the swollen resin. The resulting mixture was incubated at on a 360° rotating thermostat shaker for 15 hr at 25° C. The liquid was drained by vacuum and non-specifically bound proteins were eliminated by washing 3 times with blocking solution and 7 times with 0.1% Tween 20 in PBS, sequentially. After stringent washing, 200 mg of the assayed library resin was transferred into sample vessel of COPAS Plus (Union Biometrica) and diluted with 200 mL of 0.1% Tween 20 in PBS buffer.

Hit beads were sorted into cone-shaped wells of a 96 well plate using a COPAS Plus. Gating and sorting regions were defined for sorting beads on the COPAS Plus. The gating region was defined for beads based on their time-of-flight (TOF) and red fluorescence, and the sorting region was chosen for selecting beads based on their time-of-flight (TOF) and uniformity red fluorescence after incubation with bCAII-A647. A two step sorting strategy was used for rapid and robust sorting. The first sorting was to purify beads in a high concentration regime (>1000 beads/mL). During the first stage sorting, 200 mg (c.a. 300,000 beads) of assayed library beads in PBS were sorted using deionized water as the sheath solution. The beads in the sample cup were passed through the flow cell and focused hydrodynamically at a rate of >100 objects/s. The TOF, red fluorescence, and red fluorescence peak height of the beads were detected using a red diode laser ($\lambda$=635 nm). Due to the auto-fluorescence of the beads, the argon ion laser was intentionally turned off to minimize bleed-through effect. Less than 5,000 beads (less than 1.7% of the total beads) were collected in the first sorting. For the second step sorting, the sorted beads from the first step were thoroughly washed with deionized water and transferred to a sample cup in the COPAS Plus and diluted with 100 mL of deionized water. The beads in the sample cup were passed through the flow cell at a rate of <5 objects/s. Each hit bead was directly sorted into a 96 well plate with cone-shaped wells.

Example 3

This example demonstrates MALDI mass spectrometry of a peptide. CNBr (10 microliters, 0.50 M in 0.2 N HCl solution) was added into each well of the 96 well plate in Example 2, and the plate was purged with argon and microwaved for 1 min. The resulting solution was concentrated under centrifugal vacuum for 2 h.

To each vial or well was added CHCA (10 microliters, 0.5% solution in acetonitrile/water (70:30)) and then acetonitrile/water (10 microliters, 70:30 containing 0.1% trifluoroacetic acid (v/v)). The sample was centrifuged for 2 min and 2 microliters were withdrawn and spotted onto a 384-well MALDI-MS plate, which was allowed to stand for 15 min to allow evaporation of the sample.

Example 4

Figure 2:
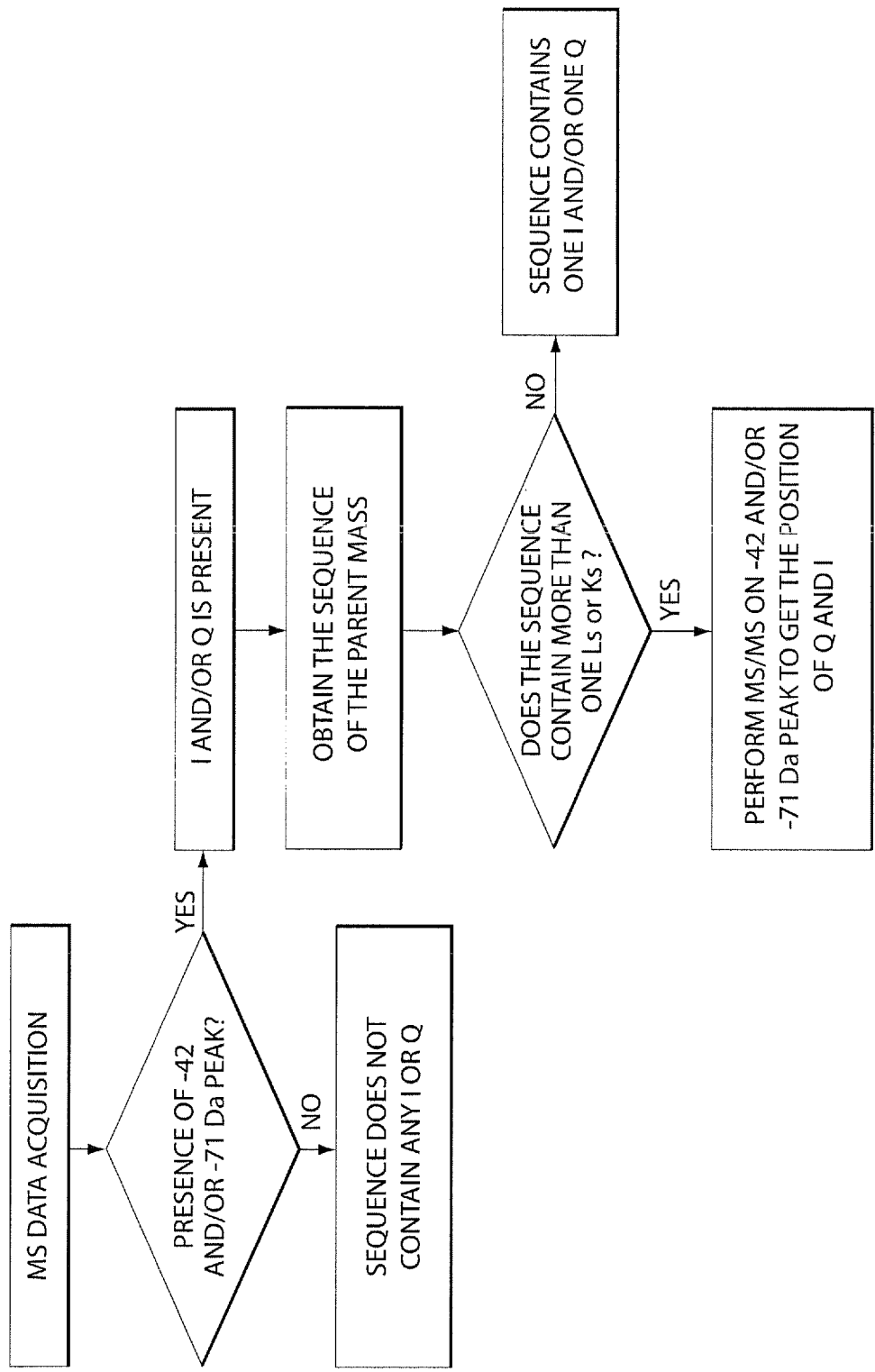
FIG. 2 shows a sequencing flowchart in accordance with another embodiment of the invention.

This example demonstrates sequencing of peptides containing isobaric amino acids using mass spectrometry. The hit peptides from the screening of the OBOC hexamer peptide library against bCAII in Example 2 were successfully sequenced by using the isobaric differentiation approach. As indicated in Example 1, glycine (G) was used as a tag for Q to differentiate between K and Q, and alanine (A) was used as a tag for I to differentiate between I and L. FIG. 2 illustrates the scheme used to obtain the full peptide sequence. An MS spectrum obtained using MALDI-TOF/TOF was first examined to identify any additional mass peaks besides the parent mass peak. In this example, a peak 42 amu smaller than the parent peak indicates that I is present in the sequence, and a peak 71 amu smaller than the parent mass peak indicates that Q is present in the sequence. The sequence of the parent peak is obtained by analysis of its MS/MS spectrum. If the sequence contains only one L/I or one K/Q, then the L/I will be I, while K/Q will be Q. However, if the parent peptide contains more than one K/Q or one L/I, then the additional mass peaks are subjected to MS/MS fragmentation to identify the position of the isobaric amino acid I or Q.

The sequencing scheme of FIG. 2 was applied to the hit peptides from screening of the hexamer library against bCAII as shown in FIG. 3. The hit peptides refer to the peptides that have binding effect with the targeted protein. The peptides from 59 hit beads were first cleaved from the bead before being subjected to mass analysis.

Figure 4A:
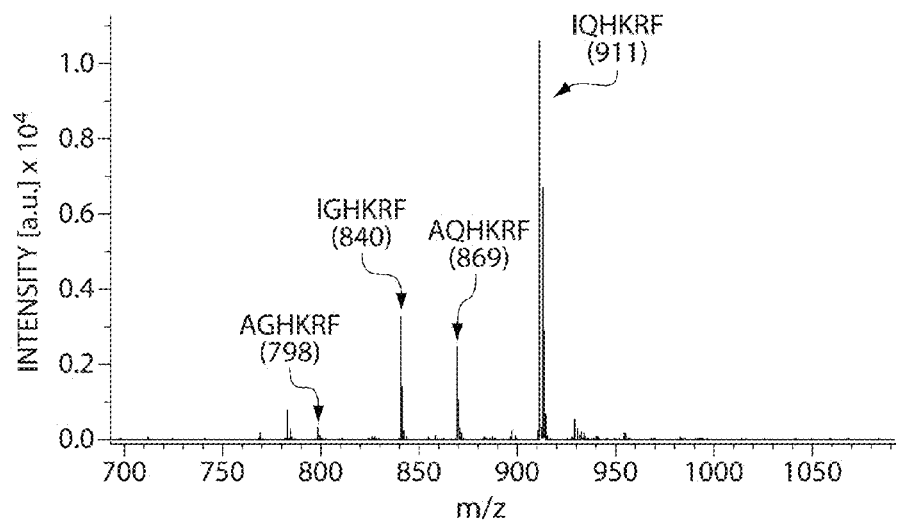
FIG. 4A shows a mass spectrum of a hit peptide (AGHKRF (SEQ ID NO: 3), IGHKRF (SEQ ID NO: 4), AQHKRF (SEQ ID NO: 5), and IQHKRF (SEQ ID NO: 1)) containing isobaric amino acids in accordance with another embodiment of the invention.
Figure 4B:
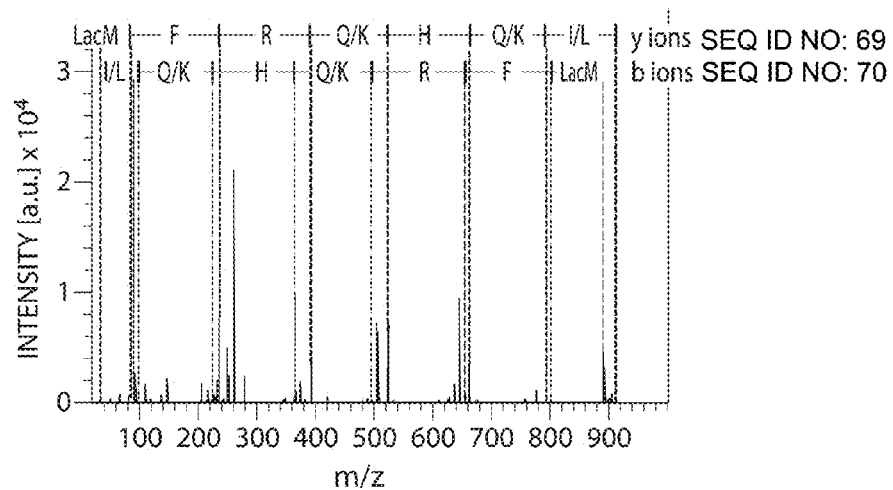
FIG. 4B shows a MALDI-TOF MS/MS spectrum of the parent peak from a hit peptide containing isobaric amino acids in accordance with an embodiment of the invention.
Figure 4C:
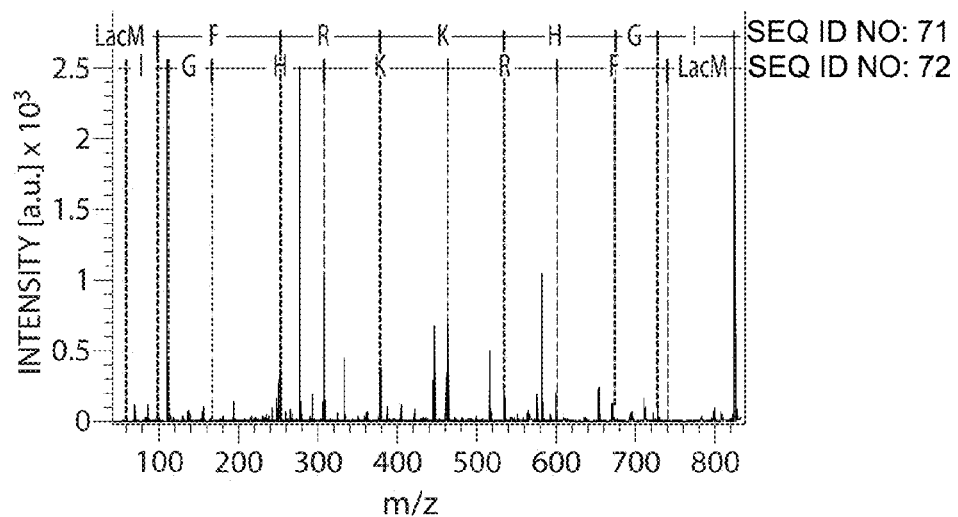
FIG. 4C shows a MALDI-TOF MS/MS spectrum of a mass peak 71 Da less than the parent peak in accordance with another embodiment of the invention.

FIGS. 4A-4C illustrate an example of the sequencing of a hit peptide containing isobaric amino acids. In FIG. 4A, the MS spectrum of a released peptide from a single bead showed two additional small peaks in addition to the parent peak. The parent peak with the highest intensity had an m/z value of 911. The other two smaller peaks had a difference of m/z −42 amu and −71 amu from the parent mass. As indicated in the analysis shown in FIG. 2, the presence of the peak with the m/z value of 869 signifies that I is present in the sequence, while the presence of the peak with the m/z value of 840 indicates that Q is present in the sequence. From the MS/MS spectrum of FIG. 4B, the sequence of the parent peptide could be determined by de novo sequencing. The peptide sequence could be determined from either a top-down or a bottom-up approach by finding the b- and the y-type ions respectively yielding (I/L)(Q/K)H(Q/K)RF (SEQ ID NO: 6). Since there is I in the peptide sequence as indicated by the −42 amu peak, the peptide sequence should be I(Q/K)H(Q/K)RF (SEQ ID NO: 8). The −42 amu mass peak does not have to undergo MS/MS fragmentation as there is only one amino acid from the I/L isobaric pair present in the parent peptide sequence. Because there is no −142 amu peak for IGHGRF (SEQ ID NO: 4), the peptide should have one Q and one K. In order to identify the position of Q in the sequence, the mass peak of 840 was subjected to MS/MS analysis. FIG. 4C shows sequencing from the MS/MS spectrum of the −71 amu peak (m/z=840). The presence of G in the peptide sequence confirms the presence of Q in that position. Consequently, the final sequence should be IQHKRF (SEQ ID NO: 1).

Example 5

This example demonstrates sequencing of peptides from a 10% cleavable OBOC peptide library, where the peptides contain isobaric amino acids. Hit peptides obtained from screening an OBOC hexamer peptide library against bCAII where only 10% of the peptides have a cleavable methionine linker group can be successfully sequenced with isobaric differentiation. Having only 10% of the peptides on a bead contain a linker group has important consequences because the linker group may influence the screening result. FIG. 5 shows 8 hit sequences from the screening.

Figure 6:
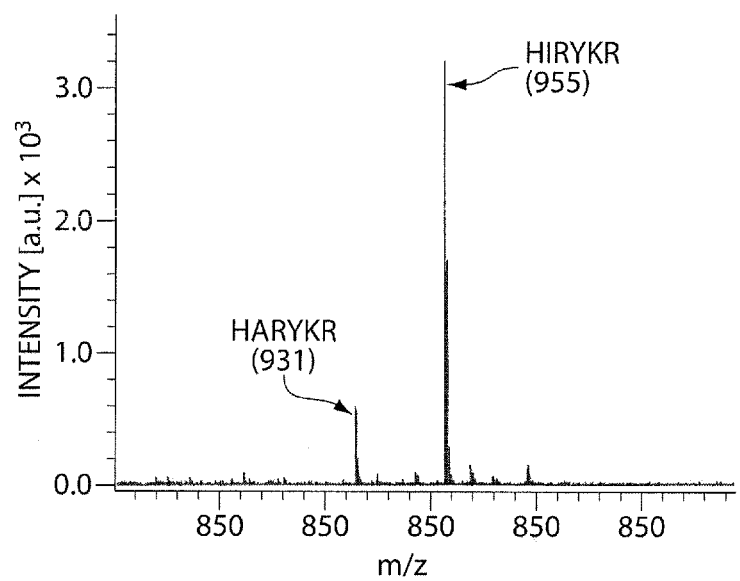
FIG. 6 shows a mass spectrum of a hit peptide (HARYKR (SEQ ID NO: 7) and HIRYKR (SEQ ID NO: 2)) containing isobaric amino acids in accordance with another embodiment of the invention.

An example of a mass spectrum of a hit peptide from the brightest bead is illustrated in FIG. 6. The sequence of the peptide (parent m/z=955) as determined by MS/MS analysis was H(I/L)RY(Q/K)R (SEQ ID NO: 73). A peak at m/z 931 that is 42 amu smaller than the parent peak indicated that I was present. The sequence was therefore read as HIRY(Q/K)R (SEQ ID NO: 74). Since there was no peak 71 amu smaller than the parent peak, Q is not present. As a result, the final peptide sequence is HIRYKR (SEQ ID NO: 2).

Figure 7:
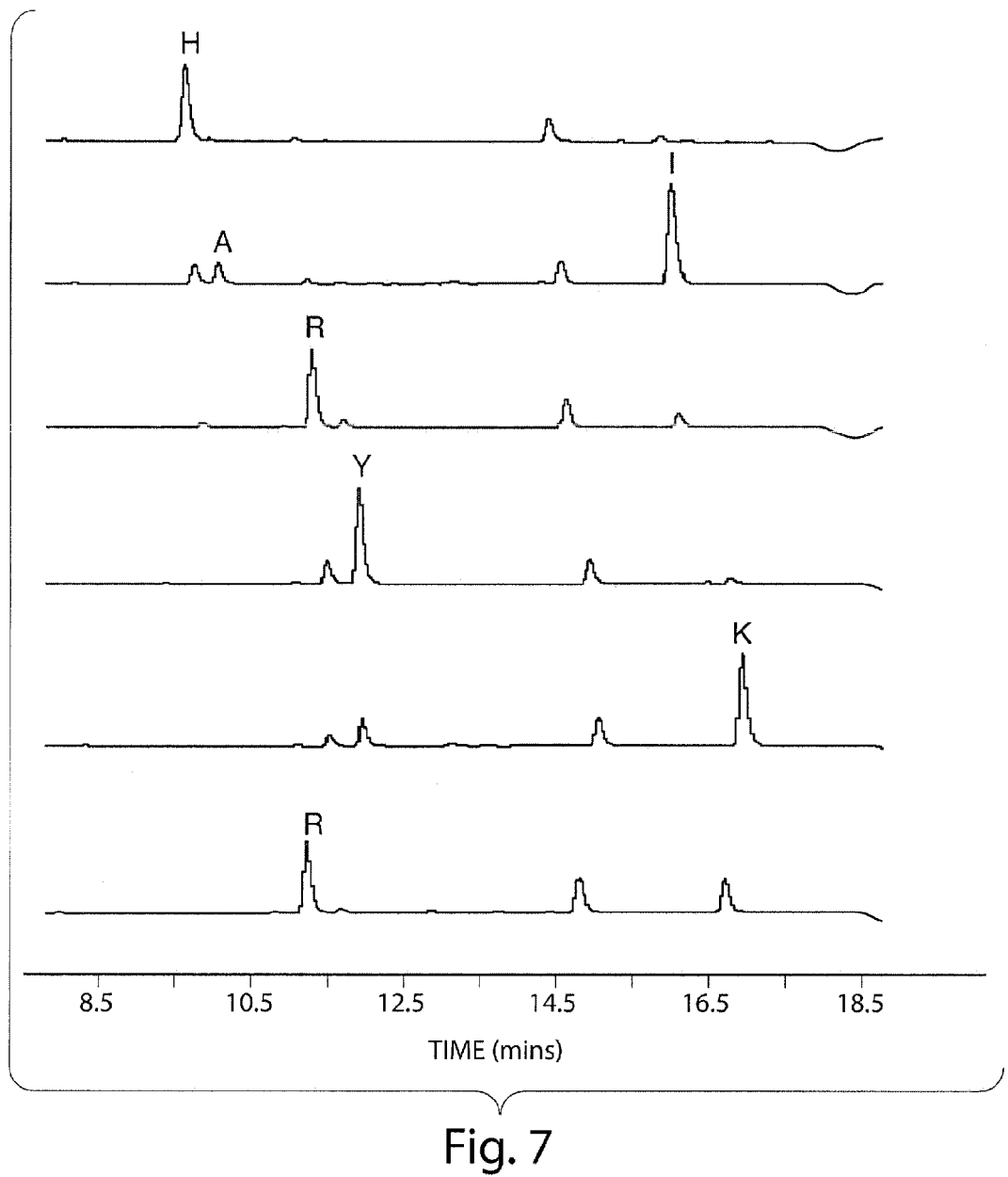
FIG. 7 shows HPLC traces from Edman degradation sequencing of a peptide in accordance with an embodiment of the invention.

This peptide sequence of HIRYKR (SEQ ID NO: 2) can be validated by Edman degradation of the remaining 90% of the peptides on the recovered bead that do not contain a cleavable linker (FIG. 7). From FIG. 7, the type and position of the amino acid present in the peptide can be identified by HPLC. Each individual HPLC spectrum was compared to amino acid standards by matching the retention time. HPLC analysis indicated that the first amino acid in the sequence is H and that the second amino acid in the sequence is I. For the second position in the peptide, a smaller peak corresponding to A is seen in the spectrum in addition to the peak corresponding to I, since 10% A was added as a tag at the coupling of I. Therefore, the peptide sequence generated with Edman degradation matches the sequence as obtained by MALDI-TOF/TOF.

The 'hit' peptide sequence of HIRYKR (SEQ ID NO: 2) was re-synthesized so that the affinity of the peptide to the protein could be determined by surface plasmon resonance (SPR). An RV well in a Titan 357 automated synthesizer (AAPPTEC) was used as a reactor. Rink Amide resins (200 mg, the loading of $NH_2$: 0.29 mmol/g) were swelled to equilibrium in NMP (5 ml) for 2 h and then solvent was drained. Fmoc-d-Arg(Pbf)-OH (2 equiv, 0.2 M solution in NMP), TBTU (2 equiv, 0.2 M solution in NMP), and DIEA (5 equiv, 0.2 M solution in NMP) were added successively, and the resulting beads were vortexed for 30 min. The coupling step was repeated using fresh portions of reagent solutions after the liquid was drained. The resulting beads were thoroughly washed by NMP (3 ml×4). Next, 20% piperidine in NMP (5 ml, v/v) was added, and the RV was vortexed for 5 min. The liquid was drained, a fresh solution of 20% piperidine in NMP (3 ml, v/v) was added, and the RV was vortexed for another 15 min. The resulting beads were thoroughly washed by NMP (3 ml×4) and DCM (3 ml×4). The coupling of the remaining amino acids was performed as described above using fmoc-d-Lys(Trt)-OH, fmoc-d-Tyr (t-Bu)—OH, fmoc-d-Arg(Pbf)-OH, fmoc-Ile-OH, and fmoc-d-His(Trt)-OH, sequentially. The beads were transferred to an 8 ml reactor equipped with a filter and incubated in 3 ml of trifluoroacetic acid (TFA)/water/triisopropylsilane (TIS) (94/3/3, v/v/v) at room temperature for 2 h. The cleavage solution was collected with another portion of TFA (3 ml) used to rinse the beads. The combined solution was nearly evaporated by using a centrifugal concentrator Gene-Vac EZ2 Plus, and diethylether (ca. 5 ml) was added to decant the crude peptide. The final purification was carried out using preparative HPLC to yield the HIRYKR (SEQ ID NO: 2) peptide having a carboxamide C-terminus as a white solid (3.5 mg, purity: >99%).

Figure 8:
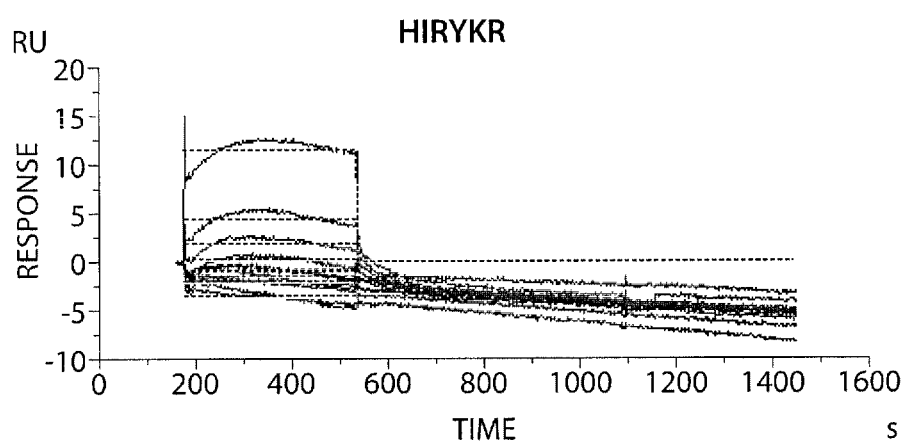
FIG. 8 shows an SPR sensorgram for the binding of HIRYKR-CONH$_2$ (SEQ ID NO: 9) to bCAII in accordance with an embodiment of the invention.

Affinity measurements were performed using a Biacore 3000 system (GE Heathcare) equipped with research grade CM5 sensor chips (GE Healthcare). The CM5 sensor chip was preconditioned after docking and priming the instrument with HBS-EP (GE Heathcare) buffer. Flow cell 1 (or 3) was used as a reference to subtract nonspecific binding, drift, and bulk refractive index. Using a flow rate of 20 microliters/min, the sensor chip's four flow cells were activated at 25° C. with a 7 min injection of amine-coupling kit (GE Healthcare) (1:1 mixture of 0.4 M EDC and 0.1 M NHS). To create a bCAII surface, 1 mg of bCAII was dissolved in 1 mL of 10 mM sodium acetate (pH 5.0) and injected across flow cell 2 only. Approximately 1000 response units (RU) of bCAII were immobilized onto this surface. Finally, 1.0 M ethanolamine (pH 8.5) was injected across the four flow cells for 4 min to deactivate the surfaces. After bCAII immobilization, the instrument was primed three times using running buffer (1×PBS+3% DMSO). HIRYKR (SEQ ID NO: 2) peptide (26.13 micrograms) was dissolved in 18 microliters DMSO and diluted with HBS-EP buffer to produce a 50 micromolar peptide stock solution. The peptide stock solution was serially diluted by a factor of 2 to a concentration of 390 nM. The concentration series of peptide solutions were injected into flow cell 2 (or 4) for 6 min using a flow rate of 30 microliters/min at 25° C. The flow cell 2 (or 4) was regenerated by Glycine 2.5 (GE Healthcare) after injection of each peptide solution. Data processing and kinetic analysis were performed using Biaevaluation software (version 4.1, Biacore). The SPR data was plotted as a function of resonance units (RUs) versus time (a sensorgram) (FIG. 8). The curves were fitted with a 1:1 Langmuir binding curve (one analyte to one ligand binding), and the dissociation constant ($K_D$) was determined to be in the micromolar range. This experiment further validates the sequencing result that the hit peptide HIRYKR (SEQ ID NO: 2) has a significant binding affinity to the protein bCAII.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An article comprising peptides attached to a surface of the article, wherein the peptides consist of:
   one or more copies of a first peptide attached to the surface of the article via a first cleavable linker, wherein the first peptide contains an isobaric amino acid from a pair of isobaric amino acids; and
   one or more copies of a second peptide attached to the surface of the article via a second cleavable linker, wherein the second peptide contains a tagging amino acid at a position corresponding to the position of the isobaric amino acid in the first peptide,
   wherein the tagging amino acid has a molecular weight different from the isobaric amino acid, wherein the second peptide is otherwise identical in length and composition to the first peptide, and wherein the N-termini of the peptides are deprotected.

2. The article of claim 1, wherein the cleavable linker is a methionine residue.

3. The article of claim 1, wherein the isobaric amino acid is leucine or isoleucine.

4. The article of claim 1, wherein the isobaric amino acid is lysine or glutamine.

5. The article of claim 1, wherein the isobaric amino acid is an unnatural amino acid.

6. The article of claim 1, wherein the tagging amino acid is an unnatural amino acid.

7. A method, comprising:
   (a) combining in a solution
      an article comprising two identical peptides attached to a surface of the article, wherein each of the peptides is attached to the surface of the article via a cleavable linker,
      an isobaric amino acid from a pair of isobaric amino acids, and
      a tagging amino acid having a molecular weight different from the amino acids of the pair of isobaric amino acid;
   (b) incubating the solution under conditions that result in incorporation of the isobaric amino acid into one of the two peptides and incorporation of the tagging amino acid into the other of the two peptides;
   (c) deprotecting the N-terminus of each of the two peptides;
   (d) cleaving the two peptides from the article; and
   (e) determining the mass of each of the two peptides, wherein a difference in mass between the two peptides is indicative of the presence of the isobaric amino acid in one of the two peptides.

8. The method of claim 7, further comprising analyzing the two peptides by mass spectrometry.

9. The method of claim 8, wherein the mass spectrometry comprises MALDI-TOF/TOF.

10. The method of claim 8, wherein analyzing the two peptides comprises sequencing the two peptides.

11. The method of claim 7, wherein the isobaric amino acid is an unnatural amino acid.

12. The method of claim 7, wherein the tagging amino acid is an unnatural amino acid.

13. The method of claim 7, wherein the tagging amino acid is glycine or alanine.

14. The method of claim 7, wherein the article is a bead.

15. The article of claim 1, wherein the article is a bead.

16. The article of claim 1, wherein the tagging amino acid is glycine or alanine.

17. A composition comprising the article of claim 1.

* * * * *

SEQUENCE LISTING

```
<160> NUMBER OF SEQ ID NOS: 74

<210> SEQ ID NO 1
<211> LENGTH: 6
<212> TYPE: PRT
<213> ORGANISM: Artificial Sequence
<220> FEATURE:
<223> OTHER INFORMATION: Synthetic Polypeptide
```

```
<400> SEQUENCE: 1

Ile Gln His Lys Arg Phe
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 2

His Ile Arg Tyr Lys Arg
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 3

Ala Gly His Lys Arg Phe
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 4

Ile Gly His Lys Arg Phe
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 5

Ala Gln His Lys Arg Phe
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is Ile or Leu
<220> FEATURE:
<221> NAME/KEY: misc_feature
<222> LOCATION: (2)..(2)
<223> OTHER INFORMATION: Xaa is Gln or Lys
<220> FEATURE:
<221> NAME/KEY: misc_feature
<222> LOCATION: (4)..(4)
<223> OTHER INFORMATION: Xaa is Gln or Lys
```

```
<400> SEQUENCE: 6

Xaa Xaa His Xaa Arg Phe
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 7

His Ala Arg Tyr Lys Arg
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa is Gln or Lys
<220> FEATURE:
<221> NAME/KEY: misc_feature
<222> LOCATION: (4)..(4)
<223> OTHER INFORMATION: Xaa is Gln or Lys

<400> SEQUENCE: 8

Ile Xaa His Xaa Arg Phe
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Modified with CONH2

<400> SEQUENCE: 9

His Ile Arg Tyr Lys Arg
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 10

Leu His Arg Tyr Arg Tyr
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 11
```

Leu His Arg Tyr Arg Arg
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 12

Leu His Arg Tyr Trp Arg
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 13

Leu His Arg Tyr Arg Lys
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 14

Leu His Arg Tyr Trp Phe
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 15

Leu His Arg Tyr Arg Gln
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 16

Leu His Arg Tyr Leu Arg
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 17

Leu His Arg Tyr Trp Tyr

```
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 18

Leu His Arg Tyr Lys Trp
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 19

Leu His Arg Tyr Trp Lys
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 20

Trp Arg Trp Arg Val Trp
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 21

Trp Arg Trp Arg Tyr Ser
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 22

Trp Arg Trp Tyr Lys Arg
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 23

Trp Arg Trp Arg Phe Lys
1               5
```

```
<210> SEQ ID NO 24
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 24

Trp Arg Trp Lys Lys Lys
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 25

Trp Arg Trp His Val Arg
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 26

Trp Arg Trp Lys Tyr Lys
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 27

Trp Arg Trp Lys Lys Val
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 28

Lys Ile Tyr Arg Phe Tyr
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 29

Lys Ile Arg Tyr Trp Arg
1               5
```

```
<210> SEQ ID NO 30
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 30

Lys Tyr Phe Lys Val Trp
1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 31

Tyr Lys Arg Tyr Trp Phe
1               5

<210> SEQ ID NO 32
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 32

Val Lys Tyr Arg Phe Tyr
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 33

Arg Arg Phe Gln Phe Tyr
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 34

Leu Arg Trp Arg Tyr Arg
1               5

<210> SEQ ID NO 35
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 35

Tyr Arg Trp Leu Arg Leu
1               5
```

```
<210> SEQ ID NO 36
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 36

Tyr Arg Trp Lys Phe Tyr
1               5

<210> SEQ ID NO 37
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 37

Tyr Leu Val Phe Arg Arg
1               5

<210> SEQ ID NO 38
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 38

Lys Ile Phe Arg Arg Arg
1               5

<210> SEQ ID NO 39
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 39

Arg Arg Trp Arg Arg His
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 40

Arg Leu Arg Arg Tyr Arg
1               5

<210> SEQ ID NO 41
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 41

Arg Gln His Trp Tyr Phe
1               5

<210> SEQ ID NO 42
```

```
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 42

Lys Arg Trp His Trp Arg
1               5

<210> SEQ ID NO 43
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 43

Trp Arg Arg Tyr Lys Lys
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 44

Arg Gln Trp His Tyr Lys
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 45

Lys Val Leu Arg Arg Leu
1               5

<210> SEQ ID NO 46
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 46

Arg Lys Trp His Tyr Gln
1               5

<210> SEQ ID NO 47
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 47

Val Trp Arg Phe Lys Lys
1               5

<210> SEQ ID NO 48
<211> LENGTH: 6
```

```
<212> TYPE: PRT
<213> ORGANISM: Artificial Sequence
<220> FEATURE:
<223> OTHER INFORMATION: Synthetic Polypeptide

<400> SEQUENCE: 48

Arg Tyr Phe Lys Gln Lys
1               5

<210> SEQ ID NO 49
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 49

Trp Arg Arg Tyr Arg Arg
1               5

<210> SEQ ID NO 50
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 50

Arg Gln Arg Arg Phe Tyr
1               5

<210> SEQ ID NO 51
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 51

Leu Arg Trp His Arg His
1               5

<210> SEQ ID NO 52
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 52

Leu Arg Tyr Arg Phe Tyr
1               5

<210> SEQ ID NO 53
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 53

Tyr Leu Arg Tyr Trp Arg
1               5

<210> SEQ ID NO 54
<211> LENGTH: 6
<212> TYPE: PRT
```

```
<213> ORGANISM: Artificial Sequence
<220> FEATURE:
<223> OTHER INFORMATION: Synthetic Polypeptide

<400> SEQUENCE: 54

Trp Lys Gln Val Tyr Arg
1               5

<210> SEQ ID NO 55
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 55

Trp Arg Tyr His Tyr Trp
1               5

<210> SEQ ID NO 56
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 56

Trp Arg Tyr Trp Arg Trp
1               5

<210> SEQ ID NO 57
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 57

Trp Arg His Gln Tyr Lys
1               5

<210> SEQ ID NO 58
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 58

Tyr His Arg Tyr Lys Arg
1               5

<210> SEQ ID NO 59
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 59

Leu Tyr Ile Arg Tyr Lys
1               5

<210> SEQ ID NO 60
<211> LENGTH: 6
<212> TYPE: PRT
<213> ORGANISM: Artificial Sequence
```

```
<220> FEATURE:
<223> OTHER INFORMATION: Synthetic Polypeptide

<400> SEQUENCE: 60

Tyr Arg Tyr Arg Ile His
1               5

<210> SEQ ID NO 61
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 61

Arg Trp Ile Trp Arg Leu
1               5

<210> SEQ ID NO 62
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 62

Arg Arg Arg Arg Arg Arg
1               5

<210> SEQ ID NO 63
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 63

Lys Lys Lys Arg Phe Arg
1               5

<210> SEQ ID NO 64
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 64

Leu Tyr Lys Lys Arg Trp
1               5

<210> SEQ ID NO 65
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 65

Tyr Lys Tyr Arg Phe Lys
1               5

<210> SEQ ID NO 66
<211> LENGTH: 6
<212> TYPE: PRT
<213> ORGANISM: Artificial Sequence
<220> FEATURE:
```

```
<223> OTHER INFORMATION: Synthetic Polypeptide

<400> SEQUENCE: 66

Arg Tyr Arg Tyr Arg Tyr
1               5

<210> SEQ ID NO 67
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 67

Arg Arg Tyr Arg Phe Arg
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 68

Arg Leu Lys Trp Arg Arg
1               5

<210> SEQ ID NO 69
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with LacM
<220> FEATURE:
<221> NAME/KEY: misc_feature
<222> LOCATION: (3)..(3)
<223> OTHER INFORMATION: Xaa is Gln or Lys
<220> FEATURE:
<221> NAME/KEY: misc_feature
<222> LOCATION: (5)..(5)
<223> OTHER INFORMATION: Xaa is Gln or Lys
<220> FEATURE:
<221> NAME/KEY: misc_feature
<222> LOCATION: (6)..(6)
<223> OTHER INFORMATION: Xaa is Ile or Leu

<400> SEQUENCE: 69

Phe Arg Xaa His Xaa Xaa
1               5

<210> SEQ ID NO 70
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is Ile or Leu
<220> FEATURE:
<221> NAME/KEY: misc_feature
<222> LOCATION: (2)..(2)
<223> OTHER INFORMATION: Xaa is Gln or Lys
<220> FEATURE:
<221> NAME/KEY: misc_feature
```

<222> LOCATION: (4)..(4)
<223> OTHER INFORMATION: Xaa is Gln or Lys
<220> FEATURE:
<221> NAME/KEY: misc_feature
<222> LOCATION: (6)..(6)
<223> OTHER INFORMATION: Modified with LacM

<400> SEQUENCE: 70

Xaa Xaa His Xaa Arg Phe
1               5

<210> SEQ ID NO 71
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with LacM

<400> SEQUENCE: 71

Phe Arg Lys His Gly Ile
1               5

<210> SEQ ID NO 72
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Modified with LacM

<400> SEQUENCE: 72

Ile Gly His Lys Arg Phe
1               5

<210> SEQ ID NO 73
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa is Ile or Leu
<220> FEATURE:
<221> NAME/KEY: misc_feature
<222> LOCATION: (5)..(5)
<223> OTHER INFORMATION: Xaa is Gln or Lys

<400> SEQUENCE: 73

His Xaa Arg Tyr Xaa Arg
1               5

<210> SEQ ID NO 74
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa is Gln or Lys -continued

```
<400> SEQUENCE: 74

His Ile Arg Tyr Xaa Arg
1               5
```